United States Patent [19]

Orban et al.

[11] 3,953,459

[45] Apr. 27, 1976

[54] PROCESS FOR THE PREPARATION OF 2,2,6,6-TETRAMETHYL-4-OXOPIPERIDINE

[75] Inventors: Ivan Orban, Basel; Hanns Lind, Liestal; Heimo Brunetti, Reinach; Jean Rody, Basel, all of Switzerland

[73] Assignee: Ciba-Geigy Corporation, Ardsley, N.Y.

[22] Filed: June 21, 1974

[21] Appl. No.: 481,921

[30] Foreign Application Priority Data

June 25, 1973 Switzerland............................ 9240/73
Apr. 19, 1974 Switzerland............................ 5438/74
May 22, 1973 Switzerland............................ 7017/73

[52] U.S. Cl. .............................................. 260/293.89
[51] Int. Cl.$^2$.......................................... C07D 211/74
[58] Field of Search ............................... 260/293.89

[56] References Cited

UNITED STATES PATENTS 3,513,170   5/1970   Murayama et al............... 260/294.7

Primary Examiner—G. Thomas Todd
Attorney, Agent, or Firm—Nestor W. Shust

[57] ABSTRACT 2,2,6,6-Tetramethyl-4-oxopiperidine is prepared from 2,2,4,4,6-pentamethyl-2,3,4,5-tetrahydropyrimidine by treatment with an acidic catalyst. Suitable catalysts are Lewis acids, protonic acids and their salts with ammonia or organic bases. The reaction may be carried out in organic solvents, preferably in acetone, by gentle heating, for example at 40° to 65°C. Yields of 95% are obtainable after a reaction of several hours.

37 Claims, No Drawings

PROCESS FOR THE PREPARATION OF 2,2,6,6-TETRAMETHYL-4-OXOPIPERIDINE

The manner of preparation of 2,2,6,6-tetramethyl-4-oxo-piperidine is already known. It comprises the reaction of 2,2,4,4,6-pentamethyl-2,3,4,5-tetrahydropyrimidine with a Lewis acid in the presence of water, as according to DT-OS No. 1,695,753. Optionally, an inert, for example protic, organic solvent can be used in addition.

On the basis of this prior art, the present invention relates to a process wherein 2,2,4,4,6-pentamethyl-2,3,4,5-tetrahydropyrimidine (acetonine) is treated with 0.2 to 12 mol%, relative to the acetonine starting material, of an acid catalyst, namely a Lewis acid catalyst or proton acid catalyst, whereby the operation is performed (a) without water or with less than the equimolar amount of water, relative to the acetonine, and in the presence of acetone and/or diacetone alcohol, or (b) with at least the equimolar amount of water, relative to the acetonine.

The reaction is optionally performed in the presence of acetone and/or diacetoneamine, triacetoneamine and/or an acid condensation product of acetone.

An acid condensation product of acetone is, for example, phorone and, in particular, mesityl oxide, and more especially diacetone alcohol.

It is advantageous to use an organic solvent.

Organic solvents particularly suitable for the process according to the invention are, for example: hydrocarbons such as aromatic hydrocarbons, e.g. benzene, toluene and xylene, as well as aliphatic hydrocarbons such as hexane, heptane and cyclohexane, as well as chlorinated hydrocarbons such as methylene chloride, trichloroethane, carbon tetrachloride, chloroform, ethylene chloride and chlorobenzene, also ethers such as tetrahydrofuran, dioxane and diethyl ether, as well as nitriles such as acetonitrile, and aprotic polar solvents such as sulpholane, nitromethane, dimethylformamide, dimethylacetamide, tetramethylurea, hexamethylphosphoric acid amide and dimethylsulphoxide, and more especially alcohols such as mono- or polyfunctional, unsubstituted or substituted aliphatic alcohols, e.g. lower alkanols such as methanol, ethanol, propanol, iso-propanol and tert.-butanol, as well as cyclohexanol, benzyl alcohol, ethylene glycol monomethyl ether, glycol and propane-1,3-diol, and also ketones such as acetone, methyl ethyl ketone and cyclohexanone. Especially suitable is a $C_1$–$C_4$-alcohol such as methanol, as well as acetone, diacetone alcohol, phorone, diacetoneamine, triacetonediamine and mesityl oxide. Equally suitable are also mixtures of the above solvents.

Compared with processes of prior art, the present process is an improvement in that, with an appreciably reduced amount of catalyst, the yield of product is greater than that obtained from hitherto known processes. This is the surprising and unexpected feature of the improvement that this process constitutes.

The catalysts which can be used according to the invention are Lewis acid catalysts: e.g. zinc chloride, tin chloride, aluminium chloride and boron trifluoride, or proton acids such as, e.g. hydrochloric acid, acetic acid, boric acid and ammonium chloride. Proton acids comprise more generally, for example, sulphonic acids and carboxylic acids, such as benzenesulphonic acid or p-toluenesulphonic acid, and formic acid, acetic acid, malonic acid, succinic acid, maleic acid, benzoic acid or cinnamic acid.

Catalysts are, in addition, salts of proton acids with ammonia or organic bases. Organic bases are, in particular, organic nitrogen bases, especially primary, secondary or tertiary nitrogen bases. Examples of such proton acids or of acid components in salts used as acid catalysts are, in particular: mineral acids such as hydrochloric acid, hydrobromic acid, hydriodic acid, nitric acid, sulphuric acid and phosphoric acid, as well as sulphonic acids such as aliphatic or aromatic sulphonic acids, e.g. methanesulphonic acid, benzenesulphonic acid, p-toluenesulphonic acid or naphthalenesulphonic acid, phosphonic acids and phosphinic acids, such as aliphatic or aromatic ones, e.g. methyl-, benzyl- or phenylphosphonic acid, or dimethyl-, diethyl- or phenylphosphinic acid, and carboxylic acids, such as monobasic, dibasic or tribasic aliphatic or aromatic carboxylic acids, e.g. saturated or unsaturated monobasic aliphatic carboxylic acids having 1–18 carbon atoms, such as formic acid, acetic acid, chloroacetic acid, dichloroacetic acid, trichloroacetic acid, cyanoacetic acid, propionic acid, butyric acid, lauric acid, palmitic acid, stearic acid, acrylic acid, methacrylic acid and cinnamic acid, saturated and unsaturated dibasic aliphatic carboxylic acids, such as oxalic acid, malonic acid, succinic acid, adipic acid, sebacic acid, tartaric acid, malic acid, fumaric acid and maleic acid, tribasic aliphatic carboxylic acids such as citric acid, monobasic aromatic carboxylic acids, such as optionally substituted benzoic acid and naphthoic acid, and dibasic aromatic carboxylic acids, such as phthalic acid and terephthalic acid. Those preferred are monobasic and dibasic aliphatic or aromatic carboxylic acids and monobasic aromatic sulphonic acids, such as acetic acid, succinic acid, maleic acid, benzoic acid, m-methylbenzoic acid, p-tert.-butylbenzoic acid, p-toluenesulphonic acid and cinnamic acid. Suitable organic bases are: aliphatic, alicyclic and aromatic, primary, secondary and tertiary amines, saturated and unsaturated nitrogen bases, urea, thiourea and basic ion exchange resins. They are thus aliphatic, primary amines, e.g. methylamine, ethylamine, n-butylamine, octylamine, dodecylamine and hexamethylenediamine, aliphatic secondary amines, e.g. dimethylamine, diethylamine, di-n-propylamine and di-isobutylamine, aliphatic tertiary amines, e.g. triethylamine, alicyclic primary amines, e.g. cyclohexylamine, aromatic primary amines, e.g. aniline, toluidine, naphthylamine and benzidine, aromatic secondary amines, e.g. N-methylaniline and diphenylamine, aromatic tertiary amines, e.g. N,N-diethylaniline, saturated and unsaturated nitrogen bases, e.g. heterocyclic bases, e.g. pyrrolidine, piperidine, N-methyl-2-pyrrolidone, pyrazolidine, piperazine, pyridine, picoline, indole, quinuclidine, morpholine, N-methylmorpholine, 1,4-diazabicyclo[2,2,2]-octane and triacetoneamine, urea, thiourea and strongly and weakly basic ion exchange resins. Preferred also is acetonine as well as diacetoneamine and triacetoneamine. Examples of preferred salts are: cyclohexylamine-formiate, pyridine-formiate, pyridine-p-toluenesulphonate, di-n-butylamineacetate, di-n-butylamine-benzoate, morpholinesuccinate, morpholine-maleate, triethylamine-acetate, triethylaminesuccinate, triethylamine-maleate, aniline-acetate, triacetoneamine-p-toluene-sulphonate and acetonine-hydrochloride.

In addition to the acid catalyst, it is possible to use co-catalysts differing from this, particularly in amounts of 0.01–0.5 mol-% relative to acetonine, e.g.: potassium iodide, sodium iodide, lithium bromide, lithium iodide, lithium rhodanide, ammonium rhodanide, lithium cyanide, lithium nitrate, ammonium sulphide, bromine, iodine, or a bromide, iodide, nitrate, methanesulphonate, benzenesulphonate or p-toluenesulphonate of ammonia, triethylamine, urea or thiourea.

Preferred catalysts are ammonium chloride and boron trifluoride. The amount of catalyst used is between 0.2 and 12 mol-%, based on the pyrimidine starting material, and is preferably between 0.2 and 7 mol-%, especially between 2 and 4 mol-%. The reaction is performed, in particular, between 40° and 120° C, preferably between 50° and 100° C. In the presence of acetone, the preferred reaction temperature is 40°–65° C, especially 50°–55°C; in the presence of diacetone alcohol or mesityl oxide it is 90°–100° C, without co-reactant addition it is preferably 50°–100° C. If ketones other than (a) acetone or (b) its acid autocondensation products are used, then the reaction temperature is advantageously −15° C to +40° C. Finally, it is also advantageous to operate under pressure, e.g. at 1–30, especially 1–10, in particular 1–3 atmospheres excess pressure.

The reaction time is preferably ½–15 hours, with acetone as co-reactant preferably 7–14 hours, particularly 8–12 hours, and with diacetone alcohol as co-reactant preferably ½–2 hours, especially 1–1½ hours.

The amount of acetone, diacetoneamine, triacetonediamine or condensation product to be used is at least 1.5 moles per mole of pyrimidine starting material; it can, however, be up to 10 moles. For practical reasons, the preferred range is 2 to 6 moles, particularly 3 to 4 moles. It is also possible, however, to use with advantage less than 1.5 moles of co-reactant.

The use of diacetone alcohol as co-reactant is particularly suitable, since the possibility of an elevated reaction temperature enables the reaction to be performed more rapidly.

The isolation can be carried out in a manner known per se, e.g. by addition of water and separation as hydrate, or by addition of acid, such as hydrochloric acid, sulphuric acid or oxalic acid, and separation as salt, or by addition of an excess of alkali especially concentrated alkali, such as aqueous sodium hydroxide solution or potassium hydroxide solution, and separation as an organic layer, or, in particular, by distillation, optionally after neutralisation of the catalyst by the addition of a base, such as sodium hydroxide, potassium hydroxide or sodium carbonate.

It is advantageous in the reaction according to the invention to use some water, as pyrimidine-hydrate water and/or as a small amount of added water. If the procedure used is according to (a), free from water, then the employed proton acid catalysts are preferably weak acids or salts thereof; if the procedure is according to (b), with water, then the employed proton acid catalysts are preferably strong acids, such as mineral acids or sulphonic acids. The water-supplying agent used can also be a hydrate of a salt.

The present invention is illustrated by the following examples.

EXAMPLE 1

172 g of 2,2,4,4,6-pentamethyl-2,3,4,5-tetrahydropyrimidine-hydrate, prepared according to data given in J. Chem. Soc. 1947, 1394, is added to a mixture of 300 g of acetone, 40 g of methanol and 0.4 g of boron trifluoride in ether solution. The resulting solution is stirred for 12 hours at 50° to 55° C and subsequently concentrated in vacuo; the resulting oil is distilled in vacuo to obtain 246 g of a slightly yellowish, partially crystallising oil, B.P.$_{12}$: 80°–86° C, which contains 228 g of 2,2,6,6-tetramethyl-4-oxo-piperidine (determined by GLC).

EXAMPLE 2

The procedure is carried out as described in Example 1, except that boron trifluoride is replaced by ammonium chloride, and the reaction product is separated as hydrate, M.P. 55°–60° C, by the addition of one mole of water per mole of product, instead of the product being distilled as in example 1.

In a further test, the product is separated as oxalate salt by neutralisation of the reaction solution with oxalic acid. In this form the product has a decomposition point of > 180° C.

EXAMPLE 3

10 g of acetonine hydrate, 10 g of diacetone alcohol and 0.3 g of ammonium chloride are mixed together and heated to about 100° C. The amount of acetonine or triacetoneamine contained in the reaction mixture is determined by gas-chromatography at regular intervals. After 1 hour reaction time at 90°–100° C, less than 5% of the original amount of acetonine is detectable. The remainder has been converted to triacetoneamine, which is isolated by fractional distillation.

EXAMPLE 4

10 g of acetonine hydrate, 10 g of acetone and 0.3 g of ammonium chloride are heated to 55° C. At regular intervals of time, a determination is made by gas-chromatography of the amount of acetonine and triacetoneamine, respectively, contained in the reaction mixture. After 12 hours reaction time at 55° C, less than 3% of the original amount of acetonine is detectable. The remainder has been converted to triacetoneamine, which is isolated by fractional distillation.

If, instead of 0.3 g of ammonium chloride, there is used in this example a mixture of 0.3 g of ammonium chloride and 0.1 mol-%, calculated on the amount of acetonine hydrate, of one of the following co-catalysts: NH$_4$Br, NH$_4$NO$_3$, NH$_4$J, LiBr, LiNO$_3$, LiJ, NaJ, KJ, J$_2$, urea nitrate, triethylammonium-p-toluenesulphonate, NH$_4$SCN, LiSCN or (NH$_4$)$_2$S, then the reaction is completed already after about 5 hours with equally good yields.

EXAMPLE 5

10 g of acetonine hydrate, 10 g of mesityl oxide and 0.3 g of ammonium chloride are heated to about 100° C. At regular intervals of time, the content of acetonine and triacetoneamine, respectively, in the reaction mixture is determined by gas-chromatography. After a reaction time of 5 hours at 90°–100° C, less than 5% of the original acetonine amount is detectable. The formed triacetoneamine is isolated by fractional distillation.

EXAMPLE 6

10 g of acetonine hydrate, 5 g of mesityl oxide, 2, 6 g of acetone and 0.3 g of ammonium chloride are heated to 55°. At regular intervals of time, the content of acetonine and triacetoneamine, respectively, in the reaction mixture is determined by gas-chromatography. After a reaction time of 12 hours at 55° C, less than 5% of the original amount of acetonine is detectable. The remainder has been re-arranged to triacetoneamine, which is isolated by fractional distillation.

EXAMPLE 7

10 g of acetonine hydrate is heated with 0.3 g of ammonium chloride to 100° C. At regular intervals of time, the content of acetonine and triacetoneamine, respectively, in the reaction mixture is determined by gas-chromatography. After 3 hours' reaction time at 100° C, less than 5% of the original amount of acetonine is detectable. The remainder has been converted to triacetoneamine, which is isolated by fractional distillation.

EXAMPLE 8

15.4 g of anhydrous acetonine, 20 g of acetone and 0.4 g of ammonium chloride are heated to 55° C. At regular intervals of time, the content of acetonine and triacetoneamine, respectively, in the reaction mixture is determined by gas-chromatography. After a reaction time of 15 hours at 55° C, at least 95% of triacetoneamine, relative to the amount of acetonine used, has been formed. After neutralisation of the catalyst with sodium hydroxide, the resulting triacetoneamine is isolated by fractional distillation.

If, instead of acetone, the same amount of diacetone alcohol or a mixture of 20 g of acetone and 0.9 g of water is used, with otherwise, the same procedure as described above, then there is obtained an approximately equally good conversion of the acetonine to triacetoneamine.

EXAMPLE 9

17.2 g of acetonine hydrate, 20 g of acetone and 0.5 g of acetic acid are heated to 55° C. At regular intervals of time, the content of acetonine and triacetoneamine, respectively, in the reaction mixture is determined by gas-chromatography. After a reaction time of 12 hours, the employed amount of acetonine hydrate has been re-arranged to triacetoneamine to the extent of 95% yield; the formed triacetoneamine is isolated by fractional distillation.

If, instead of acetic acid, there is used a corresponding amount of formic acid, benzoic acid, dichloroacetic acid, maleic acid, cinnamic acid, trichloroacetic acid, p-toluene-sulphonic acid or methanesulphonic acid, or a corresponding amount of a salt, such as ammonium bromide, triethylamine-p-toluenesulphonate, pyridineformiate, urea nitrate, triacetoneamine hydrochloride, thiourea hydrochloride, ammonium acetate, triethylamine hydrochloride or ammonium tosylate, the procedure otherwise being as described above, then triacetoneamine is obtained in similarly good yields.

EXAMPLE 10

17.2 g of acetonine hydrate, 50 g of dimethylformamide and 0.5 g of ammonium chloride are heated to 60° C. At regular intervals of time, the content of acetonine and triacetoneamine, respectively, in the reaction mixture is determined by gas-chromatography. After a reaction time of 15 hours, less than 5% of the original amount of acetonine is detectable. The remainder has been re-arranged to triacetoneamine, which is then isolated by fractional distillation.

If, instead of dimethylformamide, 40 g of dioxane, 20 g of isopropanol, 15 g of ethylene glycol monomethyl ether or a mixture of 30 g of benzene and 20 g of acetone is used, with the procedure otherwise as described above, then triacetoneamine is obtained in equally good yields.

EXAMPLE 11

17.2 g of acetonine hydrate, 30 g of methyl ethyl ketone and 0.5 g of ammonium bromide are stirred for 24 hours at 40° C. After this period of reaction, a gas-chromatographical analysis shows that about 70% of the employed amount of acetonine has been converted to triacetoneamine, which is isolated by distillation.

EXAMPLE 12

17.2 g of acetonine hydrate, 20 g of acetone, 1.8 g of water and 0.4 g ammonium chloride are heated to 55° C. After a reaction time of 12 hours, an analysis by gas-chromatography shows that at least 95% of the acetonine used has been converted to triacetoneamine, which is isolated by distillation.

If, instead of 1.8 g of water, 3.6 g or 5.4 g of water is added to the above reaction mixture, the procedure otherwise being as described there, then triacetoneamine is obtained with practically the same good yields.

EXAMPLE 13

17.2 g of acetonine hydrate, 3 g of methanol and 0.5 g of ammonium chloride are heated to 60° C. After a reaction time of 12 hours, it is shown by a gas-chromatographical analysis that about 80% of the employed amount of acetonine has been reacted to form triacetoneamine, which is isolated by distillation.

If, instead of 3 g of methanol, 2 g of water is added to the above reaction mixture, with the procedure otherwise as described above, then triacetoneamine is obtained with practically the same yields.

EXAMPLE 14

17.2 g of acetonine hydrate, 30 g of acetone and 0.5 g of ammonium chloride are heated in a sealed tube for 6 hours at 45° C. After this period of time, it is shown by gas-chromatographical analysis that at least 95% of the employed acetonine has been reacted to form triacetoneamine, which is then isolated by distillation.

What we claim is:

1. Process for the preparation of 2,2,6,6-tetramethyl-4-oxopiperidine from 2,2,4,4,6-pentamethyl-2,3,4,5-tetrahydropyrimidine (acetonine), wherein the acetonine is treated with 0.2 to 12 mol-%, relative to the acetonine starting material, of an acid catalyst, whereby the operation is performed (a) without water or with less than the equimolar amount of water, relative to the acetonine, and in the presence of acetone and/or diacetone alcohol; or (b) with at least the equimolar amount of water, relative to the acetonine.

2. Process according to claim 1, wherein the reaction is performed in the presence of an organic solvent or solvent mixture.

3. Process according to claim 2, wherein the employed solvents are ketones other than (a) acetone or (b) its acid auto-condensation products, diacetoneamine, mesityl oxide, diacetone alcohol, triacetonediamine or phorone, and the reaction is performed at −15° to +40° C.

4. Process according to claim 2, wherein the employed solvent is acetone, diacetone alcohol, mesityl oxide, diacetoneamine, triacetonediamine, phorone, a $C_1$–$C_4$-alcohol, ethylene glycol monomethyl ether, or mixtures thereof.

5. Process according to claim 4, wherein the $C_1$–$C_4$-alcohol is methanol.

6. Process according to claim 4, wherein the solvent is acetone.

7. Process according to claim 4, wherein the solvent is diacetone alcohol.

8. Process according to one of the claims 1–7, wherein the reaction is performed under elevated pressure, such as 1–30, particularly 1–10, and more especially 1–3 atmospheres.

9. Process according to claim 1, wherein the employed acid catalyst is a salt of a proton acid with ammonia or with an organic nitrogen base.

10. Process according to claim 9, wherein the employed proton acid is a mineral acid, sulphonic acid or carboxylic acid.

11. Process according to claim 10, wherein an ammonium salt is used.

12. Process according to claim 10, wherein a salt of an organic nitrogen base is used.

13. Process according to claim 12, wherein the organic nitrogen base is triacetoneamine, triethylamine, hexamethylenediamine, 1,4-diazabicyclo[2,2,2]octane urea or thiourea.

14. Process according to claim 9, wherein the proton acid is hydrochloric acid, hydrobromic acid, hydriodic acid, nitric acid, an organic sulphonic acid, formic acid or a haloacetic acid.

15. Process according to claim 9, wherein the salt of a proton acid is an ammonium salt of hydrochloric acid, hydrobromic acid, hydriodic acid, nitric acid, benzenesulphonic acid, p-toluenesulphonic acid, methanesulphonic acid, formic acid, dichloroacetic acid, trichloroacetic acid or cyanoacetic acid.

16. Process according to claim 9, wherein the salt is a salt from hydrochloric acid, hydrobromic acid, hydriodic acid, nitric acid, benzenesulphonic acid, p-toluenesulphonic acid, methanesulphonic acid, dichloroacetic acid or trichloroacetic acid, as the acid, and triacetoneamine, triethylamine, hexamethylenediamine, 1,4-diazabicyclo[2,2,2]octane, urea or thiourea, as the base.

17. Process according to claim 9, wherein the salt is ammonium chloride, ammonium bromide, ammonium iodide, ammonium formiate, ammonium tosylate, urea nitrate, urea tosylate, thiourea hydrochloride, hexamethylenediamine dihydrochloride or triacetoneamine hydrochloride.

18. Process according to claim 9, wherein the salt is hexamethylenediamine hydrochloride.

19. Process according to claim 1, wherein the acid catalyst is a Lewis acid catalyst.

20. Process according to claim 19, wherein the Lewis acid catalyst is boron trifluoride.

21. Process according to claims 1 to 7, wherein the employed acid catalyst is a proton acid catalyst.

22. Process according to claim 21, wherein the employed proton acid is a mineral acid.

23. Process according to claim 21, wherein the employed proton acid is a sulphonic acid or carboxylic acid.

24. Process according to claim 21, wherein hydrochloric acid, hydrobromic acid, hydriodic acid, nitric acid, formic acid, acetic acid, dichloroacetic acid, trichloroacetic acid, malonic acid, succinic acid, maleic acid, benzoic acid, cinnamic acid, methanesulphonic acid, benzenesulphonic acid or p-toluenesulphonic acid is used.

25. Process according to claim 1(b), wherein the employed ratio of acetonine to water is 1:1 to 1:5.

26. Process according to claims 1 to 25, wherein the co-catalyst used in addition to the catalyst is potassium iodide, sodium iodide, lithium bromide, lithium iodide, lithium rhodanide, ammonium rhodanide, lithium cyanide, lithium nitrate, ammonium sulphide, bromine, iodine, or a bromide, iodide, nitrate, methanesulphonate, benzenesulphonate or p-toluenesulphonate of ammonia, triethylamine, urea or thiourea.

27. Process according to claim 1, wherein the reaction is performed in the presence of acetone and/or diacetoneamine, triacetonediamine and/or an acid condensation product of acetone.

28. Process according to claim 27, wherein the employed acid condensation product of acetone is diacetone alcohol and/or mesityl oxide.

29. Process according to claim 27, wherein the reaction is performed with acetonine hydrate in at least 1.5 moles of acetone per mole of acetonine starting material in the presence of 0.2–7 mol-%, based on the acetonine starting material, of a Lewis acid catalyst or proton acid catalyst, at a temperature of between 40° and 65° C, in an organic protic solvent.

30. Process according to claim 29, wherein the catalyst is 0.2 to 7 mol-% of boron trifluoride, and the reaction is performed in 3 to 4 moles of acetone per mole of acetonine starting material in an organic protic solvent.

31. Process according to claim 30, wherein 0.2 to 7 mol-% of ammonium chloride is used instead of boron trifluoride.

32. Process according to one of claims 1, 2 and 4–31, wherein the reaction is performed at 40°–120° C.

33. Process according to one of claims 1, 2 and 4–28, wherein the reaction is performed at 40°–65° C.

34. Process according to one of claims 29–31, wherein the reaction is performed at 40°–65° C.

35. Process according to one of claims 27 and 28, wherein the reaction is performed in diacetone alcohol.

36. Process according to claim 1, wherein there is used, in addition to the acid catalyst, 0.01–0.5 mol-%, relative to acetonine, of a co-catalyst different from this.

37. Process according to claim 1, wherein the reaction is performed under pressure, e.g. at 1–30, particularly at 1–10, and more especially at 1–3 atmospheres excess pressure.

* * * * *